United States Patent
Maale (10) Patent No.: US 11,344,422 B2
(45) Date of Patent: *May 31, 2022

(54) GLENOID FOSSA PROSTHESIS

(71) Applicant: Gerhard E. Maale, Plano, TX (US)

(72) Inventor: Gerhard E. Maale, Plano, TX (US)

( * ) Notice: Subject to any disclaimer, the term of this patent is extended or adjusted under 35 U.S.C. 154(b) by 313 days.

This patent is subject to a terminal disclaimer.

(21) Appl. No.: 16/657,423

(22) Filed: Oct. 18, 2019

(65) Prior Publication Data

US 2020/0046510 A1 Feb. 13, 2020

Related U.S. Application Data

(63) Continuation of application No. 15/829,113, filed on Dec. 1, 2017, now Pat. No. 10,485,670, which is a (Continued)

(51) Int. Cl.
*A61F 2/40* (2006.01)
*A61B 17/17* (2006.01)
(Continued)

(52) U.S. Cl.
CPC ............ *A61F 2/4081* (2013.01); *A61B 17/15* (2013.01); *A61B 17/1778* (2016.11);
(Continued)

(58) Field of Classification Search
CPC .. A61F 2/4081; A61F 2/30767; A61F 2/4612; A61B 17/1778
See application file for complete search history.

(56) References Cited

U.S. PATENT DOCUMENTS

| 4,776,851 A | 10/1988 | Bruchman et al. |
| 5,489,309 A | 2/1996 | Lackey et al. |

(Continued)

FOREIGN PATENT DOCUMENTS

| DE | 19931670 C1 | 2/2001 |
| FR | 2776506 A1 | 1/1999 |

(Continued)

OTHER PUBLICATIONS

Derwent Abstract of DE 199 31 670 C1 Reference to Grundei, et al. (Jul. 8, 1999); Thomson Reuters; 2016.

(Continued)

*Primary Examiner* — Brian A Dukert
(74) *Attorney, Agent, or Firm* — Steven H. Washam; Washam PLLC (57) ABSTRACT

The improved glenoid fossa prosthesis for repair of a scapular deficient patient includes a base with a fixed flange, and a separable flange. A conical taper on the base and a complimentary locator edge positively orient the separable flange when joined with the base for affixation by screw. A plurality of flange fixation screws penetrates the scapular tissue between the flanges for affixation of the flanges thereto. The flange thickness is variable to approximate the topography of the scapular tissue in the affixation area to minimize tissue trimming during fitment. A cutting mask attaches to the deficient scapula in the glenoid fossa area to guide the physician in trimming scapular tissue for fitment. A cortical screw further fixates the base to the scapular tissue. A second conical taper on the base serves as a mount for a glenoid sphere (reverse shoulder) or socket (standard shoulder) repair configuration.

20 Claims, 7 Drawing Sheets

Related U.S. Application Data continuation-in-part of application No. 14/827,167, filed on Aug. 14, 2015, now Pat. No. 9,861,493.

(51) Int. Cl.
  *A61F 2/30* (2006.01)
  *A61F 2/46* (2006.01)
  *A61B 17/15* (2006.01)
  *A61B 17/86* (2006.01)

(52) U.S. Cl.
  CPC ........ *A61F 2/30767* (2013.01); *A61F 2/4612* (2013.01); *A61B 17/86* (2013.01); *A61F 2002/3092* (2013.01); *A61F 2002/3093* (2013.01); *A61F 2002/30245* (2013.01); *A61F 2002/30332* (2013.01); *A61F 2002/30433* (2013.01); *A61F 2002/30578* (2013.01); *A61F 2002/30772* (2013.01); *A61F 2002/30774* (2013.01); *A61F 2002/30962* (2013.01); *A61F 2002/4085* (2013.01)

(56) References Cited

U.S. PATENT DOCUMENTS

| | | | |
|---|---|---|---|
| 5,549,687 A | 8/1996 | Coates et al. | |
| 6,214,049 B1 | 4/2001 | Gayer et al. | |
| 6,663,670 B2 | 12/2003 | Rogers et al. | |
| 6,676,704 B1 | 1/2004 | Pope et al. | |
| 7,175,664 B1 | 2/2007 | Lakin | |
| 7,297,163 B2 | 11/2007 | Huebner | |
| 7,435,263 B2 | 10/2008 | Barnett et al. | |
| 8,292,895 B2 | 10/2012 | Bubb | |
| 8,343,226 B2 | 1/2013 | Nogarin et al. | |
| 8,986,398 B2 | 3/2015 | Poulson et al. | |
| 2007/0100458 A1* | 5/2007 | Dalla Pria | A61F 2/4081 623/19.13 |
| 2009/0319055 A1 | 12/2009 | Iversen et al. | |
| 2013/0090695 A1 | 4/2013 | Bernstein et al. | |
| 2013/0090737 A1 | 4/2013 | Flaherty et al. | |
| 2013/0123929 A1 | 5/2013 | McDaniel et al. | |
| 2014/0025173 A1 | 1/2014 | Cardon et al. | |

FOREIGN PATENT DOCUMENTS

| | | |
|---|---|---|
| WO | 2005087142 A2 | 9/2005 |
| WO | 2012051552 A2 | 4/2012 |

OTHER PUBLICATIONS

International Searching Authority; International Search Report; PCT/US2015/51036; dated Dec. 17, 2015.

International Searching Authority; Written Opinion; PCT/US2015/51036; dated Dec. 17, 2015.

R. Newsham-West, H. Nicholson, M. Walton, and P. Milburn; Long-term morphology of a healing bone-tendon interface: a histological observation in the sheep model; Journal of Anatomy; 2007; pp. 318-327; vol. 210; Anatomical Society of Great Britain and Ireland; Blackwell Publishing Ltd.; John Wiley & Sons; USA.

Robert Henshaw and Martin Malawer; Review of Endoprosthetic Reconstruction in Limb-sparing Surgery Musculoskeletal Cancer Surgery Treatment of Sarcomas and Allied Diseases; 2001; pp. 381-402; Kluwer Academic Publishers; USA.

Zimmer; Anatomical Shoulder System; Zimmer Inc.; www.zimmer.com; 2010; USA.

* cited by examiner

GLENOID FOSSA PROSTHESIS

CROSS-REFERENCE TO RELATED APPLICATIONS

This application is a continuation of U.S. patent application Ser. No. 15/829,113, filed Dec. 1, 2017, which is a continuation-in-part of U.S. patent application Ser. No. 14/827,167, filed Aug. 14, 2015, and issued as U.S. Pat. No. 9,861,493 on Jan. 9, 2018, the entirety of each incorporated herein for all purposes.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

Field Of The Invention

The present invention relates to endoprosthetic devices and, more specifically, to a scapular endoprosthetic device for full repair of the glenoid in a scapular deficient patient.

DESCRIPTION OF RELATED ART INCLUDING INFORMATION DISCLOSED UNDER 37 CFR 1.97 AND 1.98

Patients suffering from diseases or deformities of the glenoid fossa of the scapula, prior to the instant invention, have very few options for repair. Bone grafts may be utilized, relying on healthy bone (if available) from another area of the patient's body, donated bone from a cadaver, or synthetic bone in certain situations. However, such real bone grafts are limited in usefulness due to the complexities of the shoulder joint, and are problematic with regard to patient reactions to medication, bleeding, post-operative infection, and attendant pain at the harvest and graft sites. Synthetic bone, on the other hand, while reducing the incidence of rejection and post-operative infection, is limited in usefulness as well due to, again, the complexities of the shoulder joint and the physical stresses experienced therein during normal joint operation.

Current glenohumeral repair techniques include hemiarthroplasty (resurfacing or stemmed), total shoulder replacement, or reverse total shoulder replacement. Resurfacing hemiarthroplasty involves resurfacing of the humeral head joint surface with a cap-like prosthesis of highly polished metal. This is a relatively minimal repair, that relies on the existence of adequate cartilage within the glenoid fossa and a generally otherwise healthy humerus. A stemmed hemiarthroplasty involves a prosthetic humeral head joint surface with an intramedullary stem for fixation within the humeral shaft. This type of repair is often necessitated by severe fractures of the humeral head, but still requires a relatively healthy glenoid with intact cartilage surface.

Total shoulder replacement, as the name implies, involves replacement of the entire glenohumeral joint and is typically necessitated by severe arthritis, physical damage, or disease action resulting in loss of joint cartilage. In a standard total shoulder replacement, a stemmed hemiarthroplasty repair is mated with a glenoid socket prosthetic component to complete the artificial shoulder joint. The glenoid socket component is either cemented or "press-fit" into the bone of the original glenoid fossa. In a reverse total shoulder replacement scenario, the socket and ball components of the repair are reversed, such that the socket portion is fixated on the humeral head and the metal ball portion is fixated in the glenoid fossa.

The current repair methods—hemiarthroplasty and total shoulder repair—each require adequate scapular structure for support and fixation. In instances where disease process has deteriorated the scapular structure such that the glenoid fossa and surrounding bone is not viable, existing repair devices and techniques are useless. Moreover, existing repair methods that rely upon a pair of spaced fixation plates—one to affix on the remaining anterior scapular surface and the other on the remaining posterior scapular surface—do not function as intended due to the uneven thickness and curvy surface of the scapula. Such fixation plates must be sufficiently rigid to withstand the normal pressures generated by the patient's use of his/her arm or the repair will fail. If the fixation plates are malleable to allow the plates to readily conform to the scapular surface, then they are not sufficiently rigid. If the fixation plates are sufficiently rigid, and the gap therebetween is not adequate to straddle the scapula, then the surgeon must force the plates apart or must excise an even greater amount of scapular tissue than desired to complete the repair. Or, if forced onto the scapula, the latent compressive forces in the affixation area can cause post-surgical pain and other problems. If the gap therebetween is far wider than the scapular tissue thickness, then the surgeon must force the plates together during fixation. Moreover, any latent tensile forces resulting from the plates having been drawn together for affixation can, likewise, cause post-surgical pain and other problems. Either scenario exposes the patient's tissue to unnecessary pressures resulting in increased injury. What is needed is a scapular glenoid fossa replacement device to effect shoulder repair to restore patient function in such instances of scapular deficiency. Further, a need exists for a scapular glenoid fossa prosthesis with sufficiently rigid fixation plates that are modular and have stabilization features that afford fixation without application of unnecessary pressures to the prosthesis components or the patient's tissue. The present invention satisfies these needs and others as described below.

BRIEF SUMMARY OF THE INVENTION

A glenoid fossa prosthesis device for repair of a scapular deficient patient is provided, comprising: a base member including a rigid fixed flange member affixed thereto, the fixed flange member including therein at least one proximal fixation screw hole for a fixation screw and at least one distal fixation screw hole for a distal fixation screw; the base member further including a first conical taper for receiving a glenoid sphere or a glenoid socket, and a second conical taper for receiving a separable flange member; and a rigid separable flange member including a plurality of fixation screw holes therein, and a conical taper hole for receiving the second conical taper.

In one embodiment, the glenoid fossa prosthesis device fixed flange member further comprises at least one fixation screw hole differs in depth with respect to the other fixation screw holes. In another embodiment, the glenoid fossa prosthesis device fixed flange member further comprises at least one threaded fixation screw hole differs in depth with respect to the other fixation screw holes.

In another embodiment, the glenoid fossa prosthesis is provided wherein the at least one proximal fixation screw is longer than the at least one distal fixation screw.

In another embodiment, the glenoid fossa prosthesis device separable flange member further comprises a locating face for positively engaging the base member to prevent rotation of the separable flange with respect to the base member.

In another embodiment, the glenoid fossa prosthesis device base member further comprises a locating tab feature for positively engaging the separable flange member to prevent rotation of the separable flange with respect to the base member.

In another embodiment, the glenoid fossa prosthesis device fixed flange member or the separable flange member further comprises an inward surface area having a curvature that approximates a surface curvature of a patient's scapula.

In another embodiment, the glenoid fossa prosthesis device further comprises a thread engagement plate having a length-wise channel formed therein, the channel for receiving the fixed flange member or the separable flange member for engagement therewith, the thread engagement plate including a plurality of holes corresponding to the fixed flange member or separable flange member fixation screw holes.

In another embodiment, the glenoid fossa prosthesis device further comprises a thread engagement plate having a length-wise channel formed therein, the channel for receiving the fixed flange member or the separable flange member for engagement therewith, the thread engagement plate including a plurality of holes corresponding to the fixed flange member or separable flange member fixation screw holes, wherein the thread engagement plate holes are sized to engage the threads of the fixation screws to allow formation of threads within the engaged hole.

A glenoid fossa prosthesis system for repair of a scapular deficient patient is provided, comprising: a glenoid fossa prosthesis device comprising: a base member including a rigid fixed flange member affixed thereto, the fixed flange member including therein at least one proximal fixation screw hole for a fixation screw and at least one distal fixation screw hole for a distal fixation screw; the base member further including a first conical taper for receiving a glenoid sphere or a glenoid socket, and a second conical taper for receiving a separable flange member; and a rigid separable flange member including a plurality of fixation screw holes therein, and a conical taper hole for receiving the second conical taper.

In another embodiment, the glenoid fossa prosthesis system further comprises: a cutting mask device comprising a plurality of stabilizing members for positioning a locator member over a glenoid location of a scapula of a patient, and at least one cutting guide member for guiding a resection tool.

In another embodiment, the glenoid fossa prosthesis system further comprises: a first handled device comprising a pair of handles and opposing jaws, the opposing jaws adapted to engage the fixed flange member and the separable flange member near the base member.

In another embodiment, the glenoid fossa prosthesis system further comprises: a second handled device comprising a conical taper engagement member for positively engaging the first conical taper.

In another embodiment, the glenoid fossa prosthesis system further comprises: a drilling mask device comprising a lengthwise channel for engagement of the separable flange or the fixed flange, and a plurality of drill guide holes that substantially align with the separable flange or the fixed flange when engaged therewith.

In another embodiment, the glenoid fossa prosthesis system is provided wherein the at least one proximal fixation screw is of different length than the at least one distal fixation screw.

In another embodiment, the glenoid fossa prosthesis system separable flange member further comprises a locating face for positively engaging the base member to prevent rotation of the separable flange with respect to the base member.

In another embodiment, the glenoid fossa prosthesis system base member further comprises a locating tab feature for positively engaging the separable flange member to prevent rotation of the separable flange with respect to the base member.

In another embodiment, the glenoid fossa prosthesis system fixed flange member or the separable flange member further comprises an inward surface area having a curvature that approximates a surface curvature of a patient's scapula.

In another embodiment, the glenoid fossa prosthesis system further comprises a thread engagement plate having a length-wise channel formed therein, the channel for receiving the fixed flange member or the separable flange member for engagement therewith, the thread engagement plate including a plurality of holes corresponding to the fixed flange member or separable flange member fixation screw holes.

In another embodiment, the glenoid fossa prosthesis system further comprises a thread engagement plate having a length-wise channel formed therein, the channel for receiving the fixed flange member or the separable flange member for engagement therewith, the thread engagement plate including a plurality of holes corresponding to the fixed flange member or separable flange member fixation screw holes, wherein the thread engagement plate holes are sized to engage the threads of the fixation screws to allow formation of threads within the engaged hole.

The novel features that are considered as characteristic for the invention are set forth particularly in the appended claims. The invention itself, however, both as to its construction and methods of operation, together with additional objects and advantages thereof, will be best understood from the following description of specific embodiments when read with the accompanying drawings.

BRIEF DESCRIPTION OF THE SEVERAL VIEWS OF THE DRAWING(S)

The present invention will be more fully understood by reference to the following detailed description of the preferred embodiments of the present invention when read in conjunction with the accompanying drawings, wherein.

The above figures are provided for illustration and description only, and are not intended to define the limits of the disclosed invention. Use of the same reference number in multiple figures is intended to designate the same or similar parts. Furthermore, if, and when, the terms "top," "bottom," "first," "second," "upper," "lower," "height," "width," "length," "end," "side," "horizontal," "vertical," and similar terms are used herein, these terms have reference only to the structure shown in the drawing and are utilized only to facilitate describing the specific embodiment. The extension of the figures with respect to number, position, relationship, and dimensions of the parts to form the preferred embodiment will be explained or will be within the skill of the art after the following teachings of the present invention have been thoughtfully considered.

DETAILED DESCRIPTION OF THE INVENTION

A successful limb-sparing procedure for oncological purposes can be divided into three stages. The first stage involves diseased or damaged tissue resection, and must spare adequate tissue structures to support reconstruction while obtaining adequate oncologic margin to eliminate diseased tissue. The second stage involves the affixation of a stable, painless skeletal reconstruction (typically an endoprosthetic device). Third, the surrounding and supporting soft tissue is required to restore functionality to the skeletal reconstruction. The performance of the first two steps of this procedure is well understood, so it is not necessary to provide such detail herein. However, the endoprosthetic device and its use disclosed herein have heretofore never been contemplated.

As used herein, the term "scapular deficient patient" means a patient with a scapula effectively lacking a glenoid due to disease or damage. In such a patient, the original glenoid structure is severely deficient and, therefore, not viable and/or is completely non-existent due to disease, damage, or genetic deformity and, therefore, traditional shoulder repair techniques are inadequate or unworkable.

Figure 1:
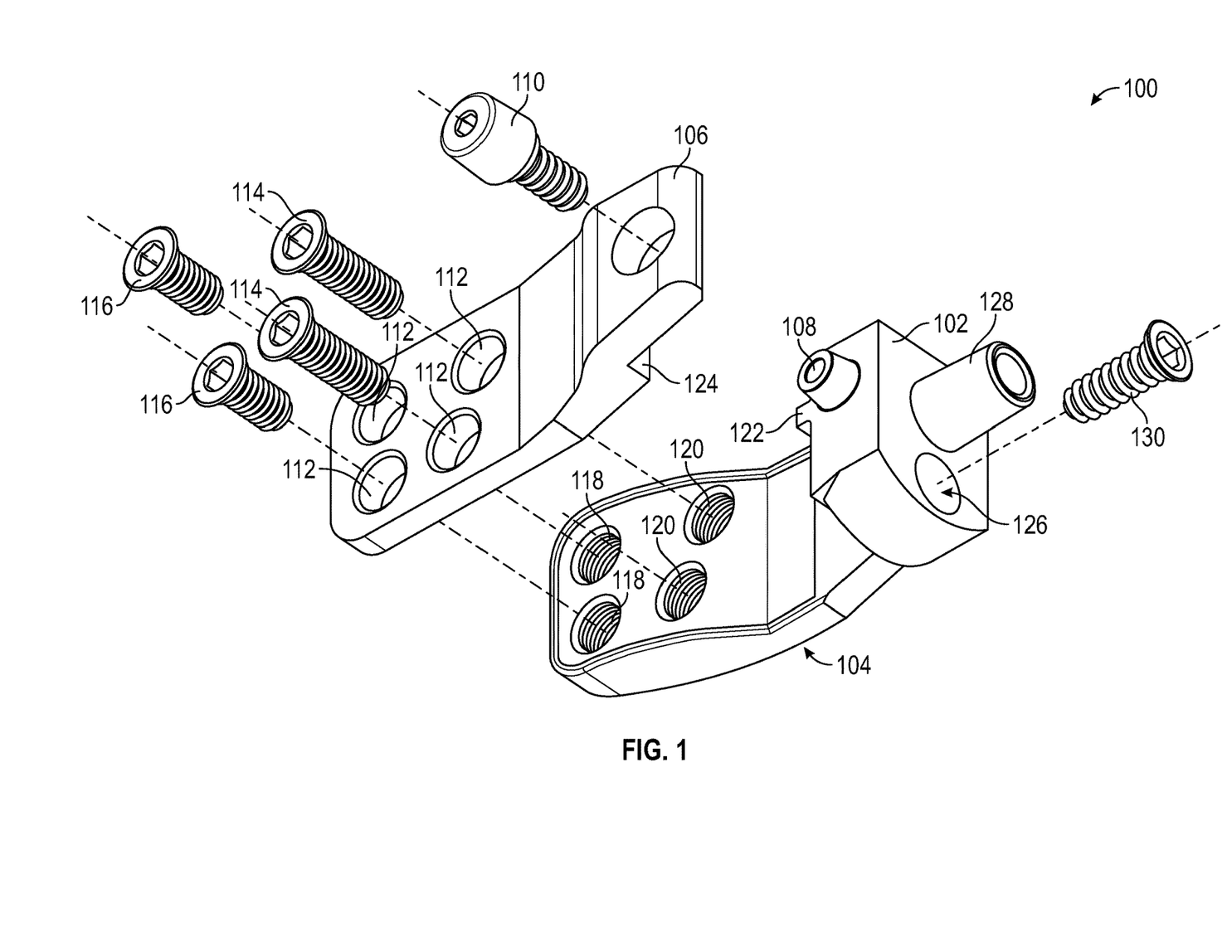
FIG. 1 is an exploded view of an embodiment of the glenoid fossa prosthesis invention illustrating the modular and stabilizing features thereof.

FIG. 1 presents an exploded view of an embodiment of the glenoid fossa prosthesis invention illustrating the modular and stabilizing features thereof. The glenoid fossa endoprosthetic device (100) includes a base member (102) with a first, primary conical taper (128) and a rigid fixed flange (104) attached thereto, and a rigid separable flange (106) for ease of fitment and affixation of the device to a patient's scapula in the glenoid deficient area. A secondary conical taper (108) acts as a stabilizing and locator member for positively locating the separable flange (106) to the base member (102), while a locating face (124) on the separable flange (106) and locating tab feature (122) on the base prevents rotation of the separable flange with respect to the attachment. An M4 screw (110) positively retains the separable flange (106) to the base (102) during affixation of the device (100).

Multiple flange fixation screws (114 and 116) are also utilized to positively retain the device (100) upon implantation. These screws (114 and 116) pass through mounting screw holes (112), through holes drilled in the remaining scapular tissue, and join with the base fixed flange mounting screw holes (118). In the present embodiment, the fixed flange (104) screw holes (118 and 120) include complimentary threads for engaging the fixation screws (114 and 116).

In another embodiment, the screw holes (118 and 120) are not threaded, but are sized such that the fixation screws (114 and 116) actively cut threads therein upon fixation. In yet another embodiment the screw holes (118 and 120) are not threaded, and pass completely through the fixed flange (104). In this embodiment, a removable thread engagement plate having a length-wise channel formed therein, provides matching screw holes into which the fixation screws (114 and 116) either form threads or engage pre-formed threads for fixation. The width of the length-wise channel allows the thread engagement plate to slip over the outer surface of the fixed flange (104) for retention thereon. In yet another embodiment the length-wise channel allows the thread engagement plate to slip over the outer surface of the separable flange (106) for retention thereon, and the fixation screws (114 and 116) are allowed to pass from the fixed flange (104) side through the separable flange (106) and into the attached thread engagement plate.

A cortical screw (130) is subsequently utilized to complete the fixation of the base (102) to the remaining scapular tissue. The first conical taper (128) is provided to position and ultimately support a glenosphere or glenosocket member (not shown).

Because the typical patient's scapula is an irregular, curving surface, the separable flange (106) and the fixed flange (104) differ in thickness as shown to compensate, thereby allowing maximum surface contact for the fixed flange to the resected scapula tissue while maintaining proper base (102) angle with regard to the patient's original glenoid. In the instant embodiment, the flange fixation screws are different lengths to compensate for this differing thickness. Two M5 screws of approximately 20 mm (114) engage the proximal screw holes (120) in the thinner portion of the fixed flange (104) while two M5 screws of approximately 17 mm (116) engage the distal screw holes (118) in the relatively thicker portion of the fixed flange (104). In another embodiment, the thick/thin portions are reversed as are the screws (114 and 116), for a specific scapular geometry. In yet another embodiment the fixed flange (104) is of even thickness, utilizing screws of same length.

A titanium trabecular mesh coating is utilized on the inner facing surfaces of the fixed flange (104) and separable flange (106). This porous mesh surface treatment creates a three-dimensional surface structure that is similar to cancellous bone, and which encourages osteoconductivity and the attachment of soft tissue. The porous mesh surface treatment is created using the known process for creating common trabecular metal, albeit with a greater porosity. For example, the surface texture may be created by thermal deposition in which the texture is effectively "printed" onto the surface atom-by-atom. Biocompatible materials, including tantalum, may be utilized in this process to create the three-dimensional surface texture structure.

The base (102) and flanges (104 and 106) are substantially rigid to resist deformation, and formed as part of a machining process. In another embodiment, the fixed flange (104)

is machined separately and otherwise attached to the base member (102) using a common metal bonding process. The machined members and all metal components of the embodiment are manufactured from biologically compatible and stable metals. In the instant embodiment, the glenosocket joint components comprise CoCrMo alloy, but may be titanium, surgical stainless steel, niobium, gold, platinum, or the like, or some alloyed combination thereof. Moreover, combinations of metals and/or biocompatible polymers and/or coatings may also be utilized and are within the scope of the claimed invention.

All or a portion of the device (100) may be created through additive manufacturing techniques, for example, using 3D printing technology. For example, it is possible to make a surface scan of the patient's scapular tissue in the area on which the device (100) is to be affixed. With the surface scan a contour map is generated that is then utilized for printing the final surface contour of the fixed flange (104) and/or the separable flange (106) members.

Figure 2:
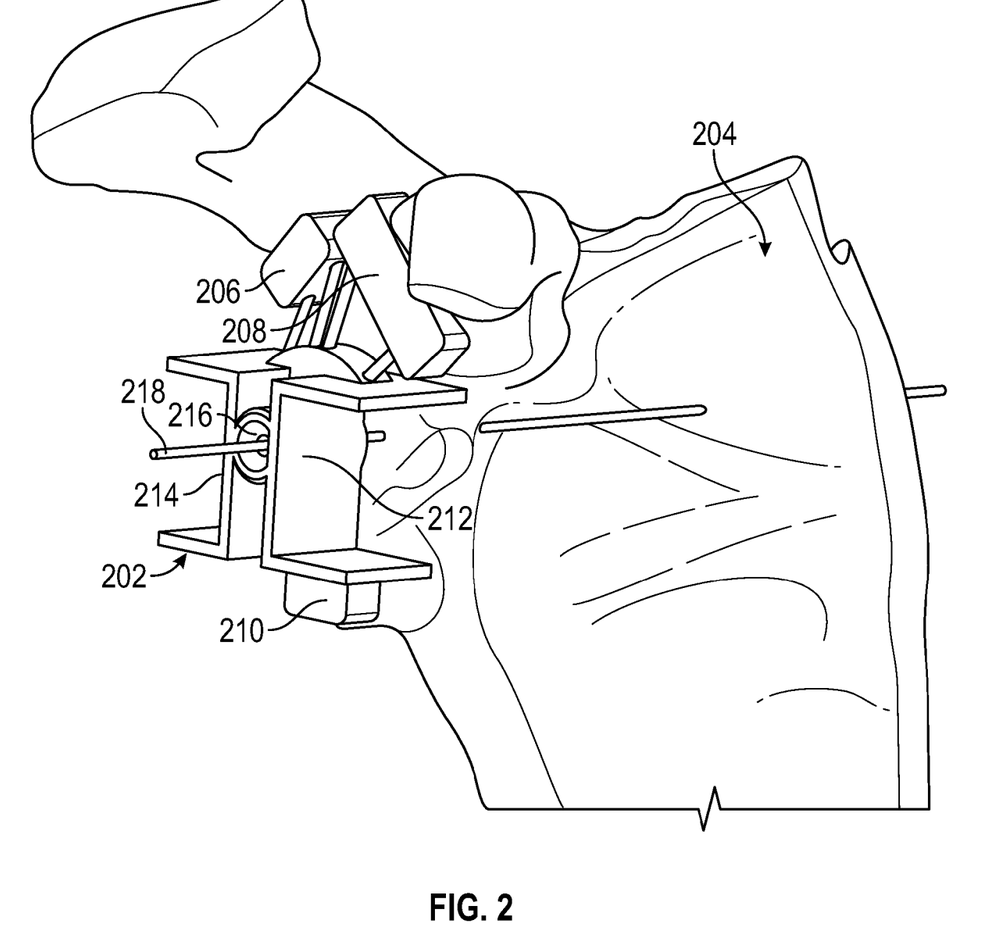
FIG. 2 is a depiction of the tools and methods utilized for preparation of a patient's scapula to accept the embodiment.

FIG. 2 is a depiction of the tools and methods utilized for preparation of a patient's scapula to accept the embodiment. A cutting mask (202) is pinned to the patient's scapula (204) as shown, centered over the patient's glenoid using a k-wire or pin (218) as a locator, passed into the original glenoid location through a locator member (216). Stabilizing members (206, 208, and 210) are positioned to further brace the cutting mask to the scapular features. An anterior cutting guide member (212) and posterior cutting guide member (214) provide a guide reference for use of resection tools to trim or cut the scapular bone and to cure the bone surface from osteophytes and tissue.

Figure 3:
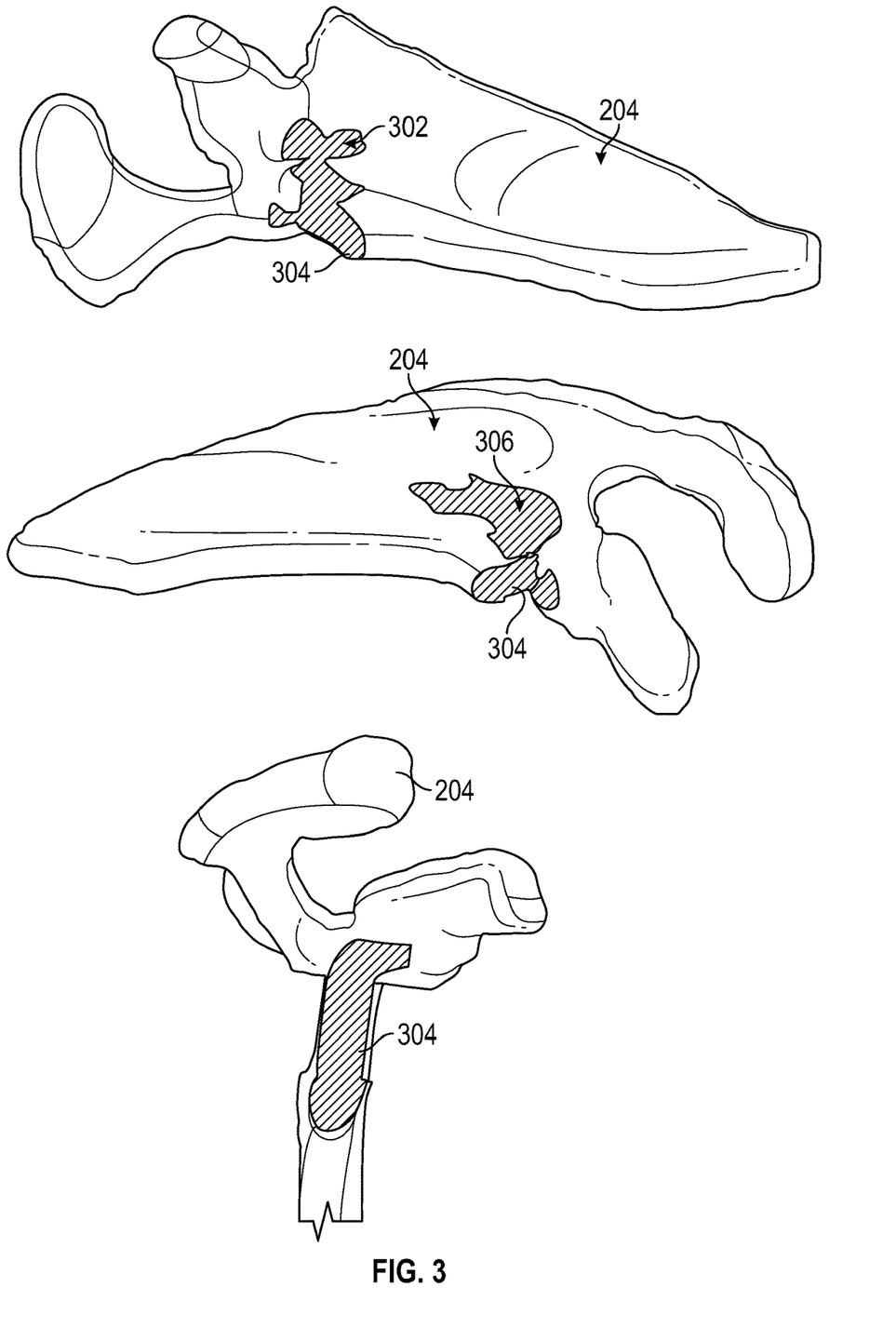
FIG. 3 is a depiction of the various sides of the scapula, prepared to accept the embodiment.

Once the scapular bone is cured of the osteophytes and tissue, the mask is removed. FIG. 3 is a depiction of the various sides of the scapula, prepared to accept the embodiment. The top image depicts the lateral and anterior faces of the scapula (204), with the anterior cut (302) and lateral cut (304) ready for placement of the base and fixed flange. The middle image depicts the lateral and posterior faces of the scapula (204), with the posterior cut (306) for placement of the separable flange member. The bottom figure depicts simply the lateral cut (304) for placement of the base member.

The base member (102) and fixed flange (104) are trial fit against the lateral cut (304) and anterior cut (302) of the scapula (204) and fit is verified. If fit is too tight, additional manual cleaning of the scapular tissue is performed to maximize the tissue contact with the base (102) and flange (104) and ensure proper angle on the base conical taper (126). The base (102) can be held by hand in place, with the separable flange (106) conical taper hole installed over the locator conical taper (108) to test fit. Additional manual cleaning of the tissue is performed to maximize the tissue contact with the separable flange (106) and to mate the flange (106) with the base (102).

Figure 4:
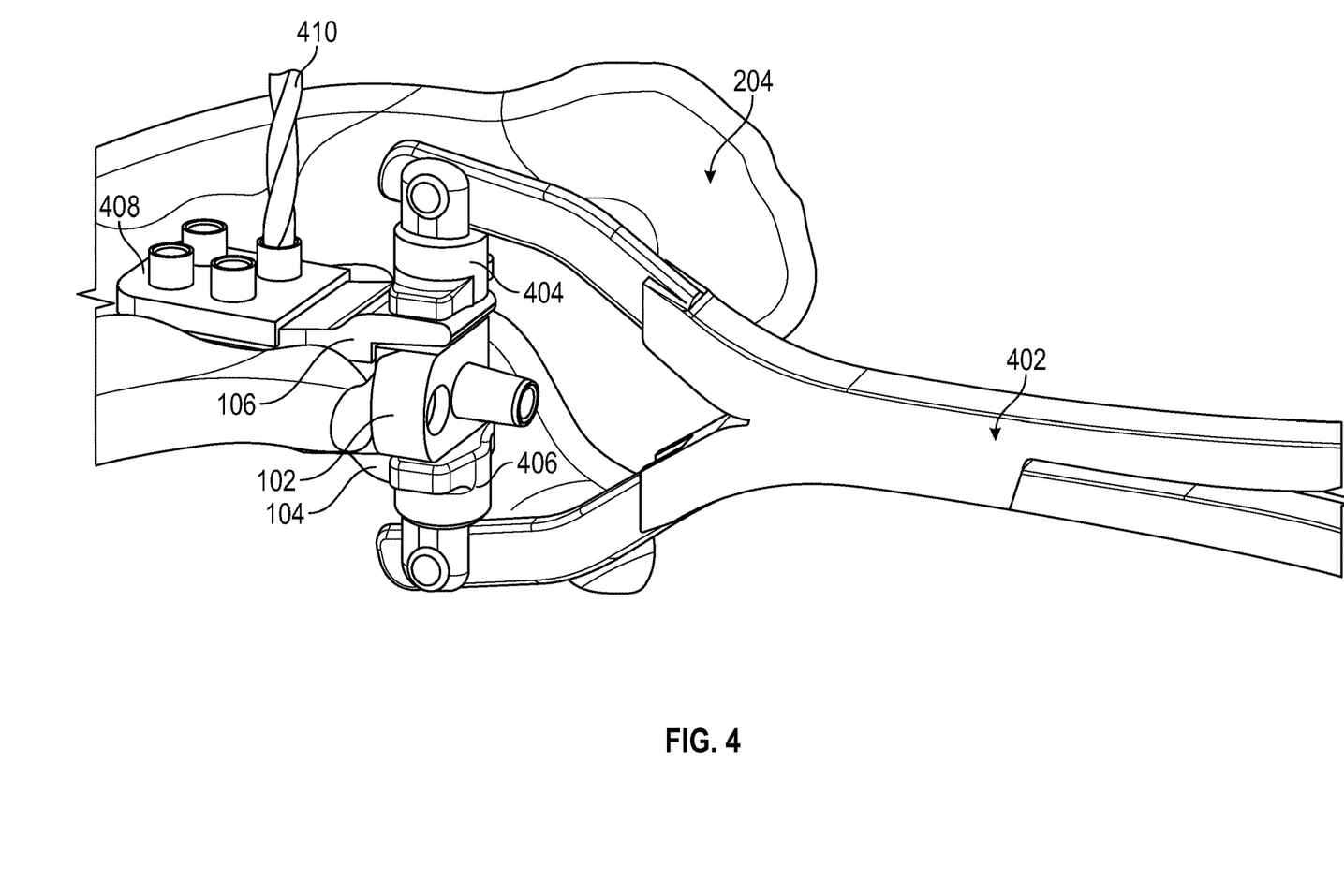
FIG. 4 is a depiction of the tools and methods utilized to stabilize the embodiment to the scapula for preparation of the affixation screw holes therein.

FIG. 4 is a depiction of the tools and methods utilized to stabilize the embodiment to the scapula for preparation of the affixation screw holes therein. A first, handled press tool (402) is provided with hinged jaws (404 and 406) that mate with complimentary features on each of the separable flange (106) and fixed flange (104) in the area of the base member (102). Squeezing the press device (402) handles causes the jaws (404 and 406) to move together in a converging direction, thereby compressing the flanges (104 and 106) and to some degree the scapular tissue therebetween. A drilling mask device (408) serves as a guide for placement of the drill bit (410) to cut appropriate screw holes in the scapular tissue. The drilling mask (408) includes a length-wise channel for positioning the mask (408) over the separable flange (106) such that the drilling mask holes substantially align with the separable flange (106) fixation screw holes thereunder. An appropriately sized drill bit (410) is rotated within each guide hole, where it is advanced until it lightly contacts the fixed flange base mounting screw holes. Once all holes are drilled, the press (402) and drilling mask (408) are removed. In yet another embodiment the drilling mask (408) may be positioned over the fixed flange (104) for formation of the holes as above.

Figure 5:
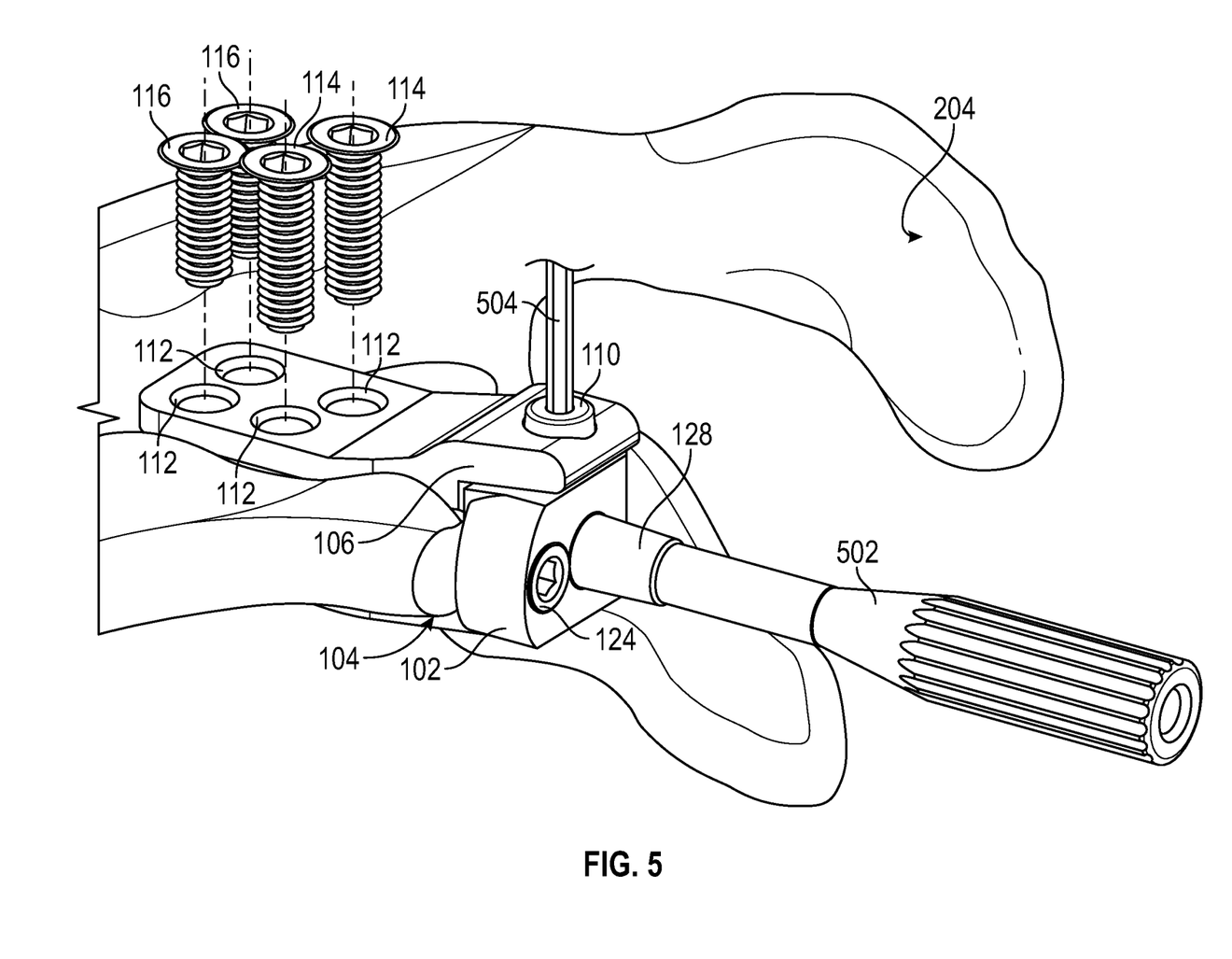
FIG. 5 is a depiction of the tools and methods utilized to affix the embodiment to the prepared scapula.

FIG. 5 is a depiction of the tools and methods utilized to affix the embodiment to the prepared scapula. Once the fitment of the flange and base to the trimmed scapula is complete and the four flange screw holes are drilled, the device is ready for permanent fixation. A second, handled impactor/extractor tool (502) is threaded onto the base (102) glenoid taper (128), where it serves as a handled counter-torque means for the surgeon to stabilize movement of the device as torque is applied to the fixation screws. In particular, the tool (502) affords a means by which torque caused by tightening (504) of the flange base taper screw (110) may be countered. This flange base screw (110) positively affixes the flange (106) to the base (102) member. Subsequently, the flange fixation screws (114 and 116) are installed and torqued as appropriate. the torque caused by tightening of the flange fixation screws (112 and 114) may also be countered with the handled tool (502). In the present embodiment, the flange base screw (110) is an M4 surgical grade screw of biocompatible material while the flange fixation screws are M5 surgical grade screws. Other embodiments may utilize similar screws, or a combination thereof.

Because the thickness and curvature of the scapula tissue in the glenoid area varies, the separable flange (106) and fixed flange (104) are likewise curved and of varying thickness to approximate the scapula topography near the glenoid. As depicted more clearly in FIG. 1, the fixed flange (104) proximal screw holes (120) require placement of a longer screw (114) than the distal screw holes (118), which require a shorter screw (116). One benefit of the longer screws (114) near the proximal end is increased thread engagement with the fixed base (104), increasing the strength of the engagement and, therefore, improving the fixation of the device (100) to the scapula (204). This can prevent subsequent post-surgical loosening of the fixation, for example, when stresses are applied by the patient to the joint during rehabilitation. In another embodiment, the separable flange (106) and fixed flange (104) are relatively even thickness and utilize same-sized flange screws (114 and 116). However, this embodiment requires substantially more effort in trimming scapular tissue for the device to achieve a flush fit.

When using an alternate embodiment of the device (100) having fixation screw holes (118 and 120) as pass-through holes, a thread engagement plate is utilized for engagement with the fixation screws (114 and 116). The thread engagement plate length-wise channel is positioned over the outer side of the fixed flange (104), which is the side of the flange opposite that of the scapular tissue. The thread engagement plate is positioned along the fixed flange (104) such that the thread engagement plate fixation screw holes align with those in the fixed flange (104), and is engaged therewith. Once in place, the fixation screws (114 and 116) engage the respective engagement plate screw hole threads, or otherwise cut or form threads therein.

Final fixation of the base is accomplished by installation of a lateral inferior cortical screw (130). In the present embodiment, the cortical screw (130) is approximately 26 mm in length or less, so as to not interfere with the proximal flange fixation screws (114). Once the cortical screw (130) is in place and appropriately torqued, the impactor/extractor handled tool (502) can be removed and the joint repair may be completed.

Figure 6:
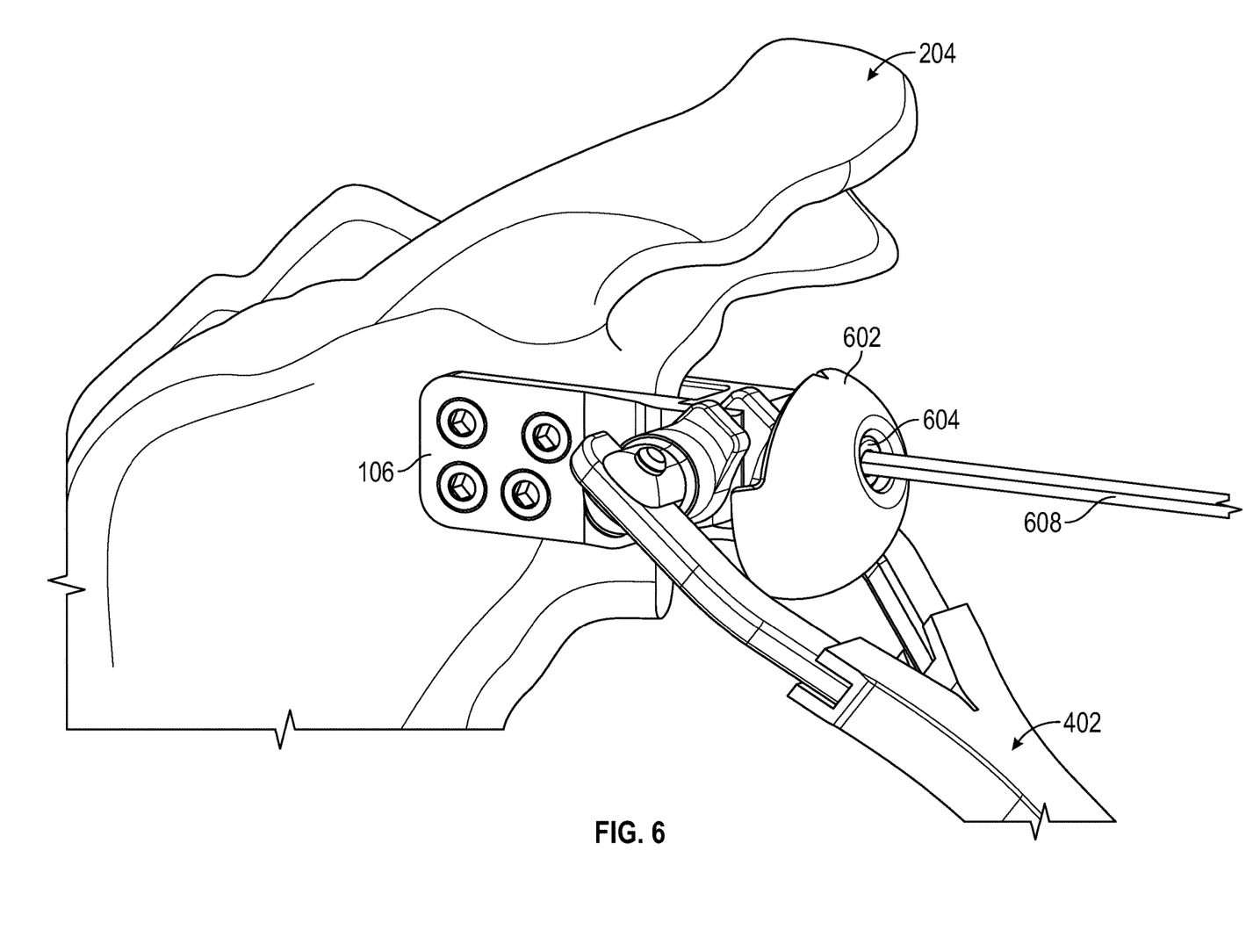
FIG. 6 is a depiction of the completion of the affixed embodiment by attachment of the glenoid sphere thereto.

FIG. 6 is a depiction of the completion of the affixed embodiment by attachment of the glenoid sphere thereto. As depicted, the glenoid sphere (602) is impacted and installed over the base taper (108). The press tool (402) is again utilized to stabilize the affixed device (106) while the glenoid screw (604) is torqued to the appropriate specification (608). In the present embodiment, the glenoid screw (604) is a customized M6 surgical grade screw of biocompatible material.

Figure 7:
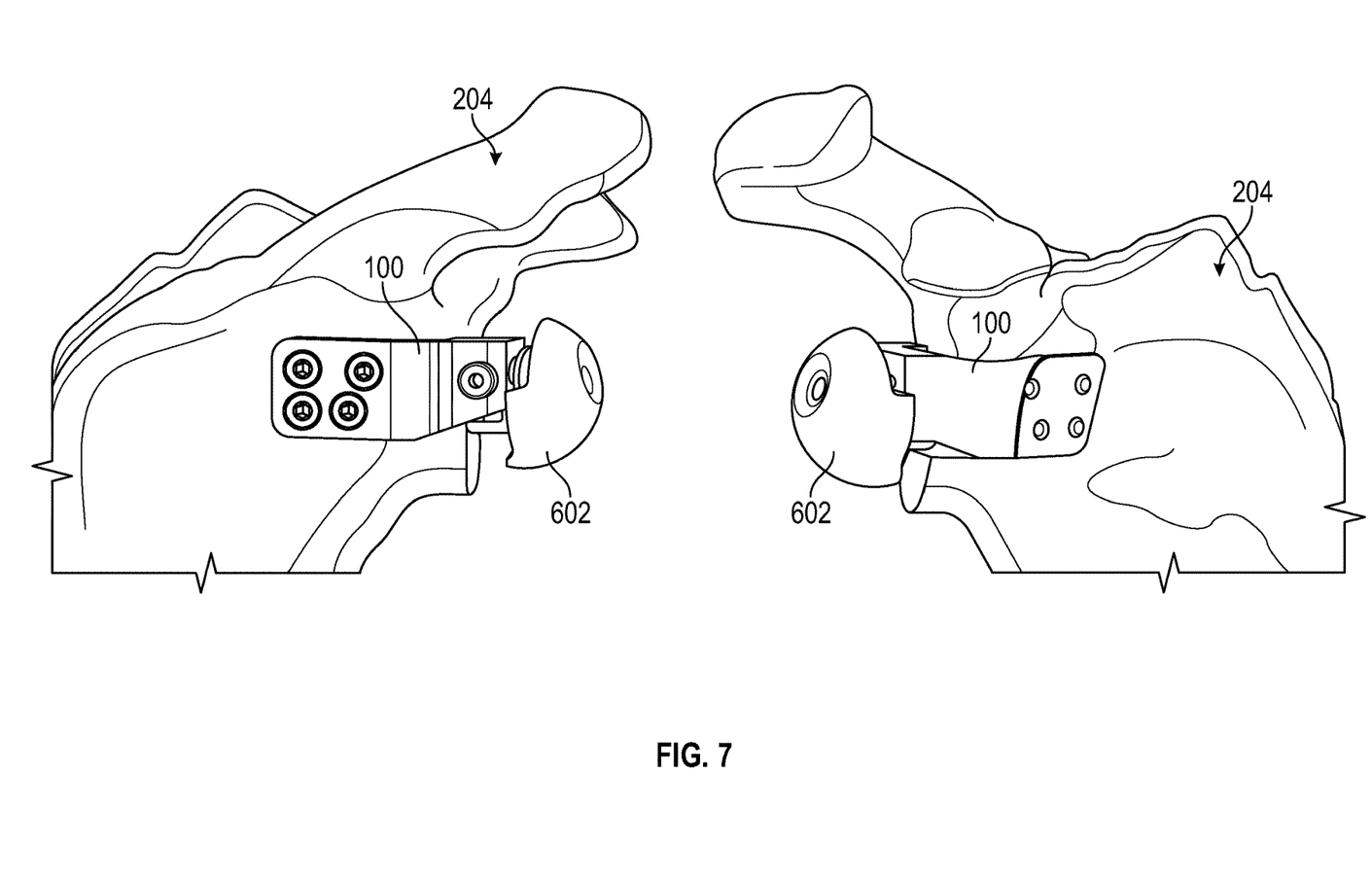
FIG. 7 is a depiction of the completed scapular repair in a reverse shoulder implant configuration.

FIG. 7 is a depiction of the completed scapular repair in a reverse shoulder implant configuration. The affixed glenoid fossa endoprosthetic device (100) with glenoid sphere (602) serves as a complete replacement for the patient's diseased or otherwise damaged, glenoid deficient scapula (204). Once affixed, the base/fixed flange/separable flange device (100) is solidly rigid on the scapular tissue on which it is attached. Maximum stability of the resulting joint is achieved through this novel approach, which provides maximum fixation strength far in excess of existing repair techniques. While this embodiment presents a reverse shoulder configuration, one of ordinary skill will understand and appreciate that a standard shoulder configuration is also contemplated and is within the scope of the claims herein.

The invention may be embodied in other specific forms without departing from the spirit or essential characteristics thereof. The present embodiments are therefore to be considered in all respects as illustrative and not restrictive. Accordingly, the scope of the invention is established by the appended claims rather than by the foregoing description. All changes which come within the meaning and range of equivalency of the claims are therefore intended to be embraced therein. Further, the recitation of method steps does not denote a limiting sequence for execution of the steps. Such method steps may therefore be performed in a sequence other than that recited unless the claim expressly states otherwise.

I claim:

1. A glenoid fossa prosthesis device for repair of a scapular deficient patient, the device comprising:
   a base member including a fixed flange member having at least one fixation screw hole therethrough for receiving a fixation screw, and a conical taper for receiving a separable flange member; and
   a separable flange member having at least one fixation screw hole therethrough for receiving a fixation screw, and a conical taper hole for receiving the conical taper,
   wherein the fixed flange and the separable flange form a channel therebetween upon engagement of the conical taper hole with the conical taper, the channel adapted to accept a patient scapula whereby each flange engages one of an anterior face or a posterior face of the scapula exclusively.

2. The glenoid fossa prosthesis device of claim 1, the fixed flange member and the separable flange member further comprising a plurality of fixation screw holes therethrough, with at least one fixation screw hole that differs in depth with respect to the other fixation screw holes.

3. The glenoid fossa prosthesis device of claim 1, the fixed flange member further comprising a plurality of fixation screw holes therethrough, with at least one threaded fixation screw hole that differs in depth with respect to the other fixation screw holes.

4. The glenoid fossa prosthesis device of claim 1, the fixed flange member and the separable flange member further comprising a plurality of fixation screw holes therethrough, wherein at least one proximal fixation screw length differs from at least one distal fixation screw.

5. The glenoid fossa prosthesis device of claim 1, the separable flange member further comprising a locating face for positively engaging the base member to prevent rotation of the separable flange with respect to the base member.

6. The glenoid fossa prosthesis device of claim 1, the base member further comprising a locating tab for positively engaging the separable flange member to prevent rotation of the separable flange with respect to the base member.

7. The glenoid fossa prosthesis device of claim 1, the fixed flange member or the separable flange member further comprising an inward surface area having a curvature that approximates a surface curvature of the scapula face with which the flange member engages.

8. The glenoid fossa prosthesis device of claim 1, the device further comprising a thread engagement plate having a lengthwise channel formed therein, the channel for receiving the fixed flange member or the separable flange member for engagement therewith, the thread engagement plate including at least one hole substantially aligned with the at least one flange member fixation screw hole on the flange with which it is engaged.

9. The glenoid fossa prosthesis device of claim 1, the device further comprising a thread engagement plate having a lengthwise channel formed therein, the channel for receiving the fixed flange member or the separable flange member for engagement therewith, the thread engagement plate including at least one hole substantially aligned with the at least one flange member fixation screw hole on the flange with which it is engaged, wherein the thread engagement plate holes are sized to engage the threads of the fixation screws to allow formation of threads within the engaged hole.

10. A glenoid fossa prosthesis system for repair of a scapular deficient patient, the system comprising:
    a glenoid fossa prosthesis device comprising:
      a base member including a fixed flange member having at least one fixation screw hole therethrough for receiving a fixation screw, and a conical taper for receiving a separable flange member; and
      a separable flange member having at least one fixation screw hole therethrough for receiving a fixation screw, and a conical taper hole for receiving the conical taper,
      wherein the fixed flange and the separable flange form a channel therebetween upon engagement of the conical taper hole with the conical taper, the channel adapted to accept a scapula of a patient whereby each flange engages one of an anterior face or a posterior face of the scapula exclusively.

11. The glenoid fossa prosthesis system of claim 10, the system further comprising:
    a cutting mask comprising:
      at least one stabilizing member for positioning the cutting mask over a glenoid location of a scapula of a patient; and
      an anterior cutting guide and a posterior cutting guide for guiding resection of the anterior face and the posterior face, respectively, of the scapula.

12. The glenoid fossa prosthesis system of claim 10, the system further comprising:
    a press tool device comprising:

a pair of handles and opposing jaws, the opposing jaws adapted to engage the fixed flange member and the separable flange member near the base member for support of the glenoid fossa prosthesis device during scapular affixation thereof.

13. The glenoid fossa prosthesis system of claim 10, the system further comprising:
an impactor/extractor tool device comprising a handled shaft and a conical taper engagement member for positively engaging the glenoid fossa prosthesis device during scapular affixation thereof.

14. The glenoid fossa prosthesis system of claim 10, the system further comprising:
a drilling mask device comprising:
a lengthwise channel for engagement of the separable flange or the fixed flange; and
a plurality of drill guide holes that substantially align with the flange with which the lengthwise channel is engaged.

15. The glenoid fossa prosthesis system of claim 10, the fixed flange member and the separable flange member further comprising a plurality of fixation screw holes therethrough, wherein at least one proximal fixation screw length differs from at least one distal fixation screw.

16. The glenoid fossa prosthesis system of claim 10, the separable flange member further comprising a locating face for positively engaging the base member to prevent rotation of the separable flange with respect to the base member.

17. The glenoid fossa prosthesis system of claim 10, the base member further comprising a locating tab for positively engaging the separable flange member to prevent rotation of the separable flange with respect to the base member.

18. The glenoid fossa prosthesis system of claim 10, the fixed flange member or the separable flange member further comprising an inward surface area having a curvature that approximates a surface curvature of the scapula face with which the flange member engages.

19. The glenoid fossa prosthesis system of claim 10, the glenoid fossa device further comprising a thread engagement plate having a lengthwise channel formed therein, the channel for receiving the fixed flange member or the separable flange member for engagement therewith, the thread engagement plate including at least one hole substantially aligned with the at least one flange member fixation screw hole on the flange with which it is engaged.

20. The glenoid fossa prosthesis system of claim 10, the glenoid fossa device further comprising a thread engagement plate having a lengthwise channel formed therein, the channel for receiving the fixed flange member or the separable flange member for engagement therewith, the thread engagement plate including at least one hole substantially aligned with the at least one flange member fixation screw hole on the flange with which it is engaged, wherein the thread engagement plate holes are sized to engage the threads of the fixation screws to allow formation of threads within the engaged hole.

* * * * *